(12) United States Patent
Wan et al.

(10) Patent No.: US 8,513,301 B2
(45) Date of Patent: Aug. 20, 2013

(54) KIND OF PIPERPHENTONAMINE HYDROCHLORIDE LYOPHILIZED POWDER FOR INJECTION AND PREPARATION AND USE THEREOF

(75) Inventors: Huayin Wan, Guangdong (CN); Rubing Li, Guangdong (CN); Yonghe Li, Guangdong (CN); Lijian Zhou, Guangdong (CN); Tieqiu Liu, Guangdong (CN); Xiaohui Zhong, Guangdong (CN)

(73) Assignee: Guangzhou Zhongwei Biotechnology Ltd., Tianhe District, Guangzhou, Guangdong (CN)

( * ) Notice: Subject to any disclaimer, the term of this patent is extended or adjusted under 35 U.S.C. 154(b) by 797 days.

(21) Appl. No.: 12/598,356

(22) PCT Filed: Jan. 31, 2007

(86) PCT No.: PCT/CN2007/000337
§ 371 (c)(1),
(2), (4) Date: Apr. 15, 2010

(87) PCT Pub. No.: WO2008/095328
PCT Pub. Date: Aug. 14, 2008

(65) Prior Publication Data
US 2010/0197731 A1    Aug. 5, 2010

(51) Int. Cl.
*A61K 31/36* (2006.01)
*A61K 31/445* (2006.01)
*A61K 9/00* (2006.01)

(52) U.S. Cl.
USPC .......................... 514/464; 514/315; 424/400

(58) Field of Classification Search
None
See application file for complete search history.

(56) References Cited

FOREIGN PATENT DOCUMENTS

| CN | 1395923 A | 2/2003 |
|----|-----------|--------|
| CN | 1396160 A | 2/2003 |
| CN | 1396162 A | 2/2003 |
| CN | 1476834 A | 2/2004 |

OTHER PUBLICATIONS

English translation of CN 1476834 A.*
English translation of CN 1476834 A. Translated on Apr. 29, 2013. Original publication Date: Feb. 25, 2004.*
International Search Report of Application No. PCTCN2007/000337 dated Oct. 18, 2007.
Written Opinion of International Searching Authority of Application No. PCTCN2007/000337 dated Oct. 18, 2007.
International Preliminary Report on Patentability dated Aug. 4, 2009.

\* cited by examiner

*Primary Examiner* — Sreeni Padmanabhan
*Assistant Examiner* — Jody Karol
(74) *Attorney, Agent, or Firm* — Buchanan Ingersoll & Rooney PC

(57) ABSTRACT

A kind of piperphentonamine hydrochloride lyophilized powder for injection and a preparation method thereof. The injection is prepared by one portion of piperphentonamine hydrochloride, 2.5-30 parts of excipient and 400-600 parts of water for injection with pH 1.5-5.5 via freeze-drying. The excipient is mannitol, dextran, lactose, saccharose, polyethylene glycol, poloxamer, glycine, etc.; It is preferred that the injection comprises one part of piperphentonamine hydrochloride, 10 parts of mannitol and 500 parts of water for injection with pH 2.0-3.0. The product is prepared by adding said piperphentonamine hydrochloride and excipient into water for injection, heating at 40° C.-90° C., ultrasonic dissolving, degerming, individually packing, pre-freezing and multistage drying, and packaging. Individually packing into a tubular glass bottle with brown color is preferred. The appearance, color & luster and solubility of the injection are excellent, the stability is good and with long storage period. The invention also provides the uses of the injection in the preparation of a medicament for treatment of heart failure and/or cardioprotection.

4 Claims, 3 Drawing Sheets

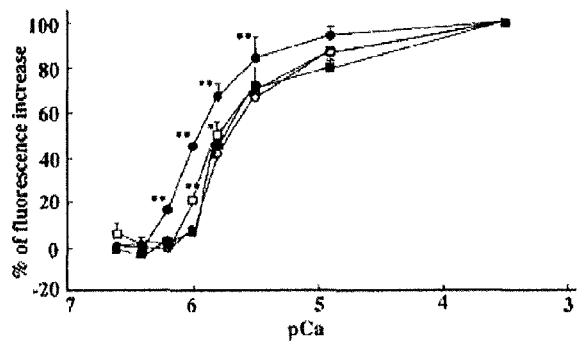
Fig. 3 o—o control , n=9 ; •—• PPTA - I 55μmol/L ; □—□ the PPTA-I 35μmol/L ;
■—■ PPTA -I 15μmol/L , mean±SD.   *p<0.05, **p<0.01 vs. control
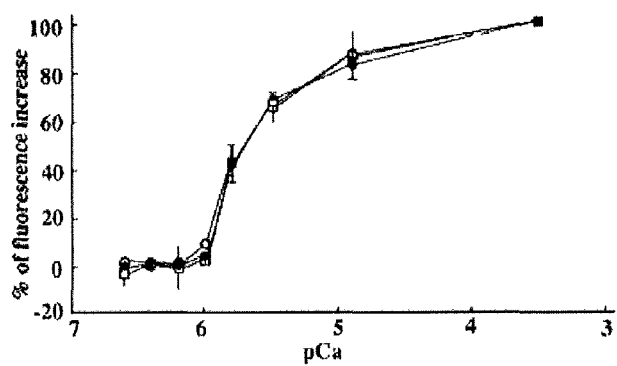
Fig. 4 o—o control , n=9 ; •—• MCI-154 , n=3 ; □—□ Sul , n=3 ; mean±SD

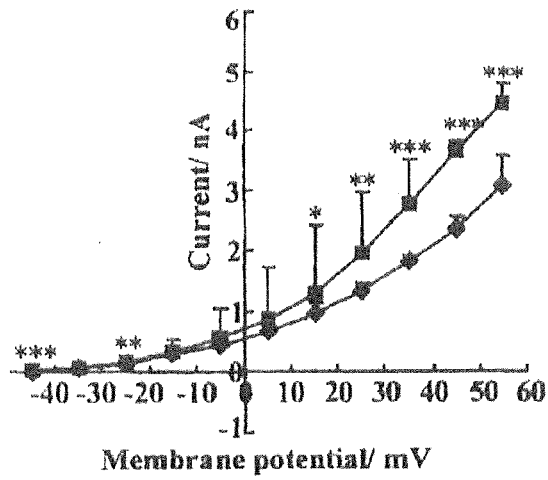
Fig. 5 ♦ control;■the PPTA-I. $^*P<0.05$, $^{}P<0.01$, $^{*}P<0.001$ vs control. n=8
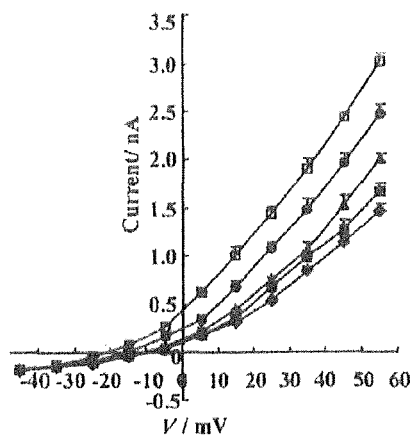
Fig. 6 ♦ control;■0.012μmol/L PPTA-I ,▲0.12μmol/L the PPTA-I ,●12μmol/L PPTA-I.
n=3

KIND OF PIPERPHENTONAMINE HYDROCHLORIDE LYOPHILIZED POWDER FOR INJECTION AND PREPARATION AND USE THEREOF

TECHNICAL FIELDS

This invention relates to a kind of piperphentonamine hydrochloride lyophilized powder for injection and preparation and use thereof. It also relates to a use of the piperphentonamine hydrochloride lyophilized powder for injection for heart failure treatment and cardioprotection for mammals, including human. The "treatment" herein means both prophylactic and therapeutic. The piperphentonamine hydrochloride lyophilized powder for injection is also known as a kind of piperphentonamine hydrochloride for injection.

BACKGROUND

Heart failure is the end-stage of cardiovascular diseases and has high death rate. Myocardial infarction and myocardial reperfusion injury are the major factors for heart failure. Although the experimental studies both in china and abroad have been revealed that calcium antagonists and free radical scavengers have effects on both treatment of myocardial infarction and protection against reperfusion injury, most calcium antagonists have limited clinical use as a result of inhibiting myocardial contraction and reducing heart function, and free radical scavengers do not have direct effect on heart function, which makes their clinical effect not fully established yet.

The therapeutic principles for heart failure are increasing heart function, vasodilating and diuretic therapy. Cardiotonics increase cardiac output by enhancing myocardial contractility to maintain the blood supply for the vital organs such as heart, brain and kidney etc. Vasodilators and diuretics decrease the load of the heart to protect heart function. However, the various cardiotonics such as cardiac glycosides, catecholamine, phosphodiesterase inhibitors (PDEI) and the like have high toxic side-effects, because they enhance the myocardial contractility mainly by increasing the concentration of intracellular calcium so as to cause proarrhythmic risk and prone to intracellular calcium overload. Although diuretics are used to be the first choice for treatment of cardiac failure, they can cause side effects such as electrolyte disturbance. Recent studies have demonstrated that angiotensin converting enzyme inhibitors (ACEI) have the effects of treating congestive heart failure and protecting cardiac muscles against ischemia and reperfusion injury, but their long term effectiveness needs to be observed.

Piperphentonamine hydrochloride (PPTA) is a novel cardiovascular chemical. The pharmacodynamic studies of PPTA demonstrated that it has good dual effects for protecting injured cardiac muscles and enhancing cardiac function with reduced myocardial oxygen consumption. PPTA increases the sensitivity of myocardial contractile proteins to $Ca^{2+}$ without increasing the calcium concentration inside the myocardial cells, even antagonizing intracellular calcium overload, thus suggests that it will not have the risk for proarrhythmia. PPTA is quickly metabolized so that it will not accumulate in the body. Concluded from the above, PPTA is calcium sensitizing cardiotonic and a myocardial protector. There has been no similar drug in the world so far. The chemical structure of Levosimendan (Simdax), the first calcium sensitizing cardiotonic in the world, marketed by Orion Corporation, Finland in 2000, has totally different from PPTA's. The systemic toxicity studies showed that PPTA is low toxic and has high therapeutic index. The raw materials required to synthesize PPTA are readily available and stable for storage under normal temperature. The synthesizing process is simple and environment friendly, and the production cost is low. The dosage form of PPTA is lyophilized powder for injection.

The Chinese Application No. 02125318.8, titled "Piperphentonamine, its salts and preparation method thereof", discloses a piperphentonamine compound, its salts and preparation method thereof, and mentions that the synthetic piperphentonamine hydrochloride has high purity and little toxic side-effect, it is promising to be developed into a novel drug for treatment of heart failure and protection against ischemia and reperfusion injury.

The Chinese Application No. 02125316.1, titled "The use of piperphentonamine and salts thereof in the preparation of a medication for treatment cardiovascular diseases", disclosed that piperphentonamine or its pharmaceutical acceptable salts can be formulated into solution, powder, tablet or capsule for intravenous injection, muscle injection and oral administration respectively, with a dosage from 0.1 to 1.0 mg/kg. But both the above patents have not described a composition and a preparation method of the piperphentonamine hydrochloride lyophilized powder for injection in detail, nor the use thereof.

The Chinese Applicaion No. 03141625.X discloses metadoxin lyophilized powder for injection and preparation method thereof. A multistage freeze-drying method for drug solution during lyophilizing process is employed, which comprises keeping the lowest temperature at −30 to −70° C. for 2 to 10 hours and rising the temperature ramped up to the highest point 0 to 70° C., keeping it for 1 to 15 hours. The temperature difference between the lowest and the highest point for freeze-drying is large and hard to control, and also makes a strict requirement for freeze-drying equipments.

DESCRIPTION OF THE INVENTION

An object of the invention is to provide a kind of piperphentonamine hydrochloride lyophilized powder for injection with good solubility, good stability and long storage period. It can act as a novel cardiotonic drug with well-defined effect, low toxicity and capability of both protecting against ischemic myocardium and improving cardiac function, so as to be used for heart failure treatment and myocardial protection in both cardiac internal medicine and cardiac surgery.

Another object of the invention is to provide a preparation method for the piperphentonamine hydrochloride lyophilized powder for injection. The freeze-dried powder for injection has good appearance after being freeze-dried, and the reconstituted drug solution has properties of acceptable solubility, clarity and color, namely, the piperphentonamine hydrochloride lyophilized powder is good stability and long storage period.

On the basis of the above objects, a piperphentonamine hydrochloride lyophilized powder for injection of the invention is prepared by the following components: 400-600 parts of water for injection with pH 1.5 to 5.5, 1 part of piperphentonamine hydrochloride, and 2.5 to 30 parts of excipient using freeze-drying The excipient is mannitol, lactose, saccharose, dextran, polyethylene glycol (PEG), Poloxamer or glycine. The pH of water for injection is adjusted by acidic solution, preferably, the pH is from 2.0 to 3.0.

The dextran used as excipient has a molecular weight in a range from 5,000 to 40,000, Dextran 20 is preferred. The PEG has a molecular weight in a range from 1,000 to 6,000, PEG 4000 is preferred. The acidic solution is hydrochloric acid, phosphate buffer or acetate buffer.

Preferably, the content of the excipient is from 5 to 20 parts.

More preferably, the content of the excipient is from 10 to 20 parts of mannitol, and most preferably, the content of the excipient is 10 parts of mannitol.

It is conventionally known that piperphentonamine hydrochloride is insoluble or poor soluble in water, the researcher of the invention finds that the piperphentonamine hydrochloride lyophilized powder for injection obtained by using conventional components and preparation method for lyophilized powder for injection will not be well shaped and will have poor solubility and stability in water for injection, it appears to be turbidity or degradation after reconstituting with water for injection, and some powder difficulty dissolved attach on the wall of the bottle. But when piperphentonamine hydrochloride and the excipient of the invention are dissolved in the water for injection with pH 1.5 to 5.5 and packaged into a brown bottle, the lyophilized powder for injection prepared via freeze-drying has good appearance, good solubility and good storage stability.

Piperphentonamine hydrochloride with the molecular formula $C_{21}H_{23}NO_4 \cdot HCl$ has a molecular weight of 89.87, batch No. 2001803, provided by Guangzhou Zhongwei Biotechnology Ltd Company. Its preparation method is described in Chinese patent No. 02125318.8. Piperphentonamine hydrochloride is difficult to be dissolved in water for injection and not stable as well, and it is easy to degrade and turn yellow. After numerous experiments, the inventors find that piperphentonamine hydrochloride treated by sonication and heating becomes easy to be dissolved in water for injection with pH 1.5 to 5.5, especially has the best solubility and stability in water for injection with pH 2 to 3. In order to achieve the lyophilized powder for injection with good redissolving ability and stability, piperphentonamine hydrochloride and excipient need to be dissolved in water for injection with pH 1.5 to 5.5 and then lyophilized, especially preferred water for injection with pH 2 to 3.

Many kinds of excipients can be used in lyophilized powder for injection, but the excipient used in the lyophilized powder for injection by intravenous administration should not affect the chemical properties of the raw materials, nor the quality detections for the powder injection. It is also required to have good solubility, capability of stuffing, and protect the active drug under the condition of low temperature and high vacuum during lyophilization. The results show that one of mannitol, lactose, saccharose, dextran, PEG, Poloxamer and glycine in an amount in a range from 2.5 to 30 times of the weight of piperphentonamine hydrochloride is proper for the invention.

Mannitol accords with the related standards of Chinese Pharmacopoeia, 2000. When the weight of Mannitol is between 2.5 and 30 times of the weight of piperphentonamine hydrochloride, especially between 5 and 20 times, more preferably from 10 to 20 times, and most preferably 10 times, the piperphentonamine hydrochloride lyophilized powder for injection prepared by the method described above has good performance on appearance, solubility, clarity and color.

The present invention also provides a preparation method for piperphentonamine hydrochloride lyophilized powder for injection by weighing piperphentonamine hydrochloride and excipient, adding 400 to 600 parts of water for injection, raising the temperature to 40 to 90° C. for ultrasonic dissolving, degerming, split charging, pre-freezing the split charged samples, multistage drying, and packaging into glass bottles.

Preferably the temperature is raised up to 60° C., dissolving under sonication, degerming by positive pressure filtering, and glass bottle is brown color.

A preferred preparation method for piperphentonamine hydrochloride lyophilized powder for injection comprises: weighing piperphentonamine hydrochloride and excipient, adding 500 parts of water for injection for dissolution, degerming, split charging, decreasing the temperature of the sample chamber to −25-−35° C. at first, and placing the split charged samples into it for pre-freezing for 3 to 7 hours, then raising up to −20-−10° C. for freeze dehydrating for 15 to 25 hours, and again raising up to 20-30° C. for drying for 5 to 15 hours.

A preferred embodiment of the method comprises: decreasing the temperature of the sample chamber to −30° C. at first and placing the split charged samples into it for pre-freezing for 5 hours, then raising up to −15° C. for freeze dehydrating for 20 hours, and again raising up to 25° C. for drying for 10 hours, that is called pre-freezing method with fast freezing. The freeze-drying curve is showed in FIG. 1.

Another preferred preparation method for piperphentonamine hydrochloride lyophilized powder for injection comprises: weighing piperphentonamine hydrochloride and excipient, adding 500 parts of water for injection for dissolution, degerming, split charging in brown bottles, placing the split charged samples into the sample chamber, then decreasing the temperature of the sample chamber to −25-−35° C. for pre-freezing for 2 to 4 hours, then raising up to −20-−10° C. for freeze dehydrating for 15 to 25 hours, and again raising up to 20-30° C. for drying for 5 to 15 hours, capping and packaging.

A preferred embodiment of the method comprises: placing the split charged samples into the sample chamber, then decreasing the temperature of the sample chamber to −30° C. for pre-freezing for 3 hours, then raising up to −15° C. for freeze dehydrating for 20 hours, and again raising up to 25° C. for drying for 10 hours, capping and packaging. That is called pre-freezing method with slow freezing. The freeze-drying curve is showed in FIG. 2.

The sample appearances will be largely differed by different freeze-drying processes used in the preparation of piperphentonamine hydrochloride lyophilized powder for injection. But the freeze-drying process of the invention eliminates the differences among the freeze-dried samples. The obtained product is well shaped and has desirable freeze-drying effect.

The present invention also provides another preparation method for piperphentonamine hydrochloride lyophilized powder for injection. The inventors performed freeze-dying process under the different conditions, resulting in that the obtained lyophilized powder for injection has poor appearance stability. In order to achieve good stability and save energy as well, the inventors had made many efforts to select freeze-drying processes described above.

The appearance, solubility and clarity of the samples hasn't significant difference by either the pre-freezing method with fast freezing showed in FIG. 1 or the pre-freezing method with slow freezing showed in FIG. 2. The temperature range between the lowest and highest point is suitable for freeze-drying compared with that the one described in the above Chinese patent No. 03141625.X, which is easy to control and will not lead to a strict requirement for the equipments. The energy consumption is less than that in the reference.

The lyophilized powder for injection obtained by the above methods will not have significant influence on the detection of piperphentonamine hydrochloride, and not interfere with the content measurement by HPLC. All of the appearance, solubility and clarity of the lyophilized powder are acceptable.

After numerous repeated experiments, the product of piperphentonamine hydrochloride lyophilized powder for injection obtained by the preparation method of the invention has the properties of content uniformity, weight variation and moisture content meeting with the quality standards for piperphentonamine hydrochloride for injection.

The piperphentonamine hydrochloride freeze-dried powder obtained by the above method is placed into a brown bottle, said freeze-dried powder is not prone to degrade, the storage period of which is two years under light-proof condition at room temperature.

The pharmacology studies performed for the lyophilized powder for injection demonstrated that: the formulation is a calcium sensitizer for myocardial cells and a potassium channel agonist for vascular smooth muscle cells, which has treatment effects on heart failure and myocardial injury.

BRIEF DESCRIPTION OF THE DRAWING

FIG. 3 The effects of the different concentrations of piperphentonamine hydrochloride on the fluorescence affinity curve of cTn C to $Ca^{2+}$.

FIG. 4 The effect of 50 μmol of MCI-154 and Sul on the fluorescence affinity curve of cTn C to $Ca^{2+}$.

FIG. 5 The effect of 0.1 μmol/L of PPTA-I on the current-voltage curve of whole cell Ca2+-sensitive-potassium channel.

FIG. 6 The effect of 0.01-10 μmol of PPTA-I on the current-voltage curve of whole cell Ca2+-sensitive-potassium channel.

EMBODIMENT

Figure 1:
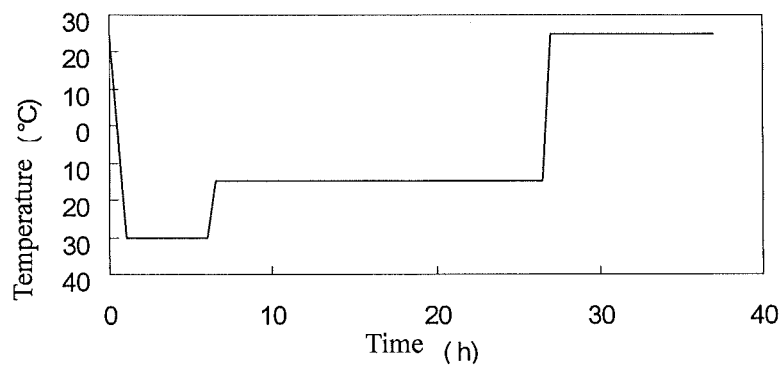
FIG. 1 The freeze-drying curve of piperphentonamine hydrochloride for pre-freezing method with fast freezing.
Figure 2:
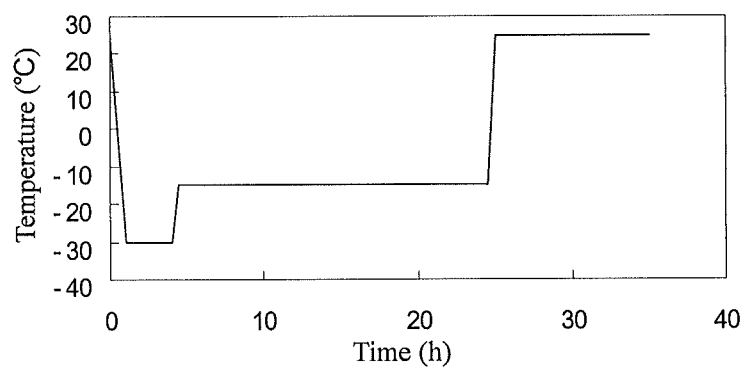
FIG. 2 The freeze-drying curve of piperphentonamine hydrochloride for pre-freezing method with slow freezing.

The following examples are used to illustrate the method and the use of the formulation, however, it should be understand that the present invention is not limited to these examples.

Example 1

Example 1 comprises the steps of: weighing 1.0 g of piperphentonamine hydrochloride and 2.5 g of mannitol as excipient, placing them into a flask and adding 400 ml of water for injection with pH 1.5 adjusted by 1N hydrochloric acid solution for homogenizing. Raising the temperature up to 40° C. and ultrasonic dissolving till the materials fully dissolved (about 10 minutes), degerming by positive pressure filtering using stainless steel filter, split charging by 5 ml per vial, half covered by a special rubber plug for lyophilization. Decreasing the temperature of the sample chamber to −25° C., placing the samples into it for pre-freezing for 3 hours, then increasing the temperature to −20° C. for freeze dehydrating for 15 hours, again increasing the temperature to 20° C. for drying for 5 hours. The properties of the resulted product are as follows:

| Detection Items | | | | |
| --- | --- | --- | --- | --- |
| Appearance | pH | Color | Clarity | Solubility |
| Shaped, loosened by fillip with slightly forcing, without shrinkage | 2.0 | YG1-2 | 0.5 | Easy to dissolve in water |

Example 2

Example 2 comprises the steps of: weighing 1.0 g of piperphentonamine hydrochloride and 10.0 g of mannitol as excipient, placing them into a flask and adding 500 ml of water for injection with pH 2.0 adjusted by 1N hydrochloric acid solution, homogenizing. Raising the temperature up to 50° C. and ultrasonic dissolving until the materials fully dissolved (about 10 minutes), degerming by positive pressure filtering using stainless steel filter, split charging by 5 ml per vial, and half covering with a special rubber plug for lyophilization. Decreasing the temperature of the sample chamber to −30° C., placing the samples into it for pre-freezing for 5 hours, then increasing the temperature to −20° C. for freeze dehydrating for 20 hours, again increasing the temperature to 25° C. for drying for 10 hours. The properties of the resulted product are as follows:

| Detection Items | | | | |
| --- | --- | --- | --- | --- |
| Appearance | pH | Color | Clarity | Solubility |
| White, whole loose cake | 2.5 | YG1-2 | 0.5 | Easy to dissolve in water |

Example 3

Example 3 comprises the steps of: weighing 1.0 g of piperphentonamine hydrochloride and 20 g of mannitol as excipient, placing them into a flask and adding water for injection with pH 2.5 adjusted by 1N hydrochloric acid solution to 600 ml, homogenizing. Raising the temperature up to 55° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the sample chamber, then decreasing the temperature of the sample chamber to −30° C. for pre-freezing for 4 hours, then increasing the temperature to −20° C. for freeze dehydrating for 15 hours, again increasing the temperature to 20° C. for drying for 5 hours. The properties of the resulted product are as follows: shaped, good appearance, not changing shape by a fillip with slightly forcing, easy to dissolve, clear, and color YG1-2.

Example 4

Example 4 comprises the steps of: weighing 1.0 g of piperphentonamine hydrochloride and 30 g of mannitol as excipient, placing them into a flask and adding water for injection with pH 3.0 adjusted by 1N hydrochloric acid solution to 600 ml, homogenizing. Raising the temperature up to 60° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the sample chamber, then decreasing the temperature of the sample chamber to −25° C. for pre-freezing for 3 hours, then increasing the temperature to −15° C. for freeze dehydrating for 20 hours, again increasing the temperature to 25° C. for drying for 10 hours. The properties of the resulted product are as follows: shaped, good appearance, not changing shape by a fillip with slightly forcing fillip, easy to dissolve, clear, and color YG1-2.

Example 5

Example 5 comprises the steps of: weighing 1.0 g of piperphentonamine hydrochloride and 25 g of mannitol as excipient, placing them into a flask and adding water for injection with pH 3.5 adjusted by acetic acid-ammonium acetate buffer to 500 ml, homogenizing. Raising the temperature up to 65° C. and ultrasonic dissolving until the materials fully dissolved (about 10 minutes), degerming by positive pressure filtering using stainless steel filter, split charging by 5 ml per vial, half covering a special rubber plug for lyophilization. Placing the split charged samples into the sample chamber, then decreasing the temperature of the sample chamber to −35° C. for pre-freezing for 2 hours, then increasing the temperature to −10° C. for freeze dehydrating for 25 hours, again increasing the temperature to 30° C. for drying for 15 hours. The properties of the resulted product are as follows: shaped, good appearance, not changing shape by a slightly forced fillip, easy to dissolve, clear, and color YG1-2.

Example 6

Example 6 comprises the steps of: weighing 1.0 g of piperphentonamine hydrochloride and 10.0 g of mannitol as excipient, adding water for injection with pH 3.0 adjusted by 1N hydrochloric acid solution to 500 ml. Raising the temperature up to 70° C. and ultrasonic dissolving until the materials fully dissolved (about 10 minutes), degerming by positive pressure filtering using stainless steel filter, split charging by 5 ml per vial, half covering with a special rubber plug for lyophilization. Placing the split charged samples into the sample chamber, then decreasing the temperature of the sample chamber to −20° C. for pre-freezing for 3 hours, then increasing the temperature to −15° C. for freeze dehydrating for 20 hours, again increasing the temperature to 25° C. for drying for 10 hours. The properties of the resulted product are as follows:

| Detection Items | | | | |
| --- | --- | --- | --- | --- |
| Appearance | Color and luster | Solubility | Clarity | Moisture content (%) |
| Whole loosed cake | White | Dissolved in 30 seconds | 0.5 | 2.4 |

Example 7

Example 7 comprises the steps of: weighing 1.0 g of piperphentonamine hydrochloride and 2.5 g of saccharose as excipient, placing them into a flask and adding 400 ml of water for injection with pH 4.0 adjusted by acetic acid-ammonium acetate buffer, homogenizing. Raising the temperature up to 70° C. and ultrasonic dissolving until the materials fully dissolved (about 10 minutes), decoloring with active carbon and leaching the active carbon, degerming by positive pressure filtering using stainless steel filter, split charging by 5 ml per vial, and half covering with a special rubber plug for lyophilization. Decreasing the temperature of the sample chamber to −35° C., placing the samples into it for pre-freezing for 7 hours, then increasing the temperature to −20° C. for freeze dehydrating for 25 hours, again increasing the temperature to 30° C. for drying for 15 hours. The properties of the resulted product are as follows:

| Detection Items | | | | |
| --- | --- | --- | --- | --- |
| Appearance | pH | Color | Clarity | Solubility |
| Shaped, not changing shape by a fillip with slightly forcing | 4.4 | YG1-2 | 0.5 | Easy to dissolve in water |

Example 8

Example 8 comprises the steps of: weighing 1.0 g of piperphentonamine hydrochloride and 30 g of saccharose as excipient, placing them into a flask and adding 600 ml of water for injection with pH 4.5 adjusted by acetic acid-ammonium acetate buffer, homogenizing. Raising the temperature up to 80° C. and ultrasonic dissolving until the materials fully dissolved, decoloring by active carbon adsorption and leaching the active carbon, degerming by positive pressure filtering using stainless steel filter, split charging by 5 ml per vial, and half covering with a special rubber plug for lyophilization. Decreasing the temperature of the sample chamber to −25° C., placing the samples into it for pre-freezing for 3 hours, then increasing the temperature to −10° C. for freeze dehydrating for 25 hours, again increasing the temperature to 30° C. for drying for 15 hours. The properties of the resulted product are as follows:

| Detection Items | | | | |
| --- | --- | --- | --- | --- |
| Appearance | pH | Color | Clarity | Solubility |
| Shaped, acceptable appearance | 4.5 | YG1-2 | 0.5 | Easy to dissolve in water |

Example 9

Example 9 comprises the steps of: weighing 1.0 g of piperphentonamine hydrochloride and 20 g of saccharose as excipient, placing them into a flask and adding 500 ml of water for injection with pH 5.0 adjusted by acetic acid-ammonium acetate buffer, homogenizing. Raising the temperature up to 85° C. and ultrasonic dissolving until the materials fully dissolved (about 10 minutes), decoloring by active carbon adsorption and leaching the active carbon, degerming by positive pressure filtering using stainless steel filter, split charging by 5 ml per vial, and half covering with a special rubber plug for lyophilization. Placing the samples into the sample chamber, then decreasing the temperature of the sample chamber to −30° C. for pre-freezing for 3 hours, then increasing the temperature to −15° C. for freeze dehydrating for 20 hours, again increasing the temperature to 25° C. for drying for 10 hours. The properties of the resulted product are as follows:

| Detection Items | | | | |
|---|---|---|---|---|
| Appearance | pH | Color | Clarity | Solubility |
| Shaped, acceptable appearance | 5.1 | YG1-2 | 0.5 | Easy to dissolve in water |

Example 10

Example 10 comprises the steps of: weighing 1.0 g of piperphentonamine hydrochloride and 10 g of saccharose as excipient, placing them into a flask and adding 400 ml of water for injection with pH 5.5 adjusted by disodium hydrogen phosphate-sodium dihydrogen phosphate buffer, homogenizing. Raising the temperature up to 90° C. and ultrasonic dissolving until the materials fully dissolved (about 10 minutes), decoloring by active carbon adsorption and leaching the active carbon, degerming by positive pressure filtering using stainless steel filter, split charging by 5 ml per vial, and half covering with a special rubber plug for lyophilization. Placing the samples into the sample chamber, then decreasing the temperature of the sample chamber to −35° C. for pre-freezing for 4 hours, then increasing the temperature to −20° C. for freeze dehydrating for 15 hours, again increasing the temperature to 20° C. for drying for 5 hours. The properties of the resulted product are as follows:

| Detection Items | | | | |
|---|---|---|---|---|
| Appearance | pH | Color | Clarity | Solubility |
| Shaped, acceptable appearance | 5.5 | YG1-2 | 0.5 | Easy to dissolve in water |

Example 11

Example 11 comprises the steps of: weighing 1.0 g of piperphentonamine hydrochloride and 2.5 g of dextran-20 as excipient, placing them into a flask and adding 400 ml of water for injection with pH 2.0 adjusted by 1N hydrochloric acid solution, homogenizing. Raising the temperature up to 55° C. and ultrasonic dissolving until the materials fully dissolved (about 10 minutes), degerming by positive pressure filtering using stainless steel filter, split charging by 5 ml per vial, and half covering with a special rubber plug for lyophilization. Decreasing the temperature of the sample chamber to −35° C., then placing the split charged samples into it for pre-freezing for 7 hours, then increasing the temperature to −20° C. for freeze dehydrating for 15 hours, again increasing the temperature to 20° C. for drying for 5 hours. The properties of the resulted product are as follows:

| Detection Items | | | | |
|---|---|---|---|---|
| Appearance | pH | Color | Clarity | Solubility |
| White, loosed cake, hardly changing shape and shrinkage | 2.5 | YG1-2 | 1.0 | Easy to dissolve in water |

Example 12

Example 12 comprises the steps of: weighing 1.0 g of piperphentonamine hydrochloride and 10 g of dextran-20 as excipient, placing them into a flask and adding 500 ml of water for injection with pH 3.0 adjusted by 1N hydrochloric acid solution, homogenizing. Raising the temperature up to 60° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the sample chamber, then decreasing the temperature to −25° C. for pre-freezing for 3 hours, then increasing the temperature to −10° C. for drying for 15 hours, again increasing the temperature to 20° C. for drying for 5 hours. The properties of the resulted product are as follows:

| Detection Items | | | | |
|---|---|---|---|---|
| Appearance | pH | Color | Clarity | Solubility |
| White, loosen cake, hardly changing shape and shrinkage | 3.5 | YG1-2 | 1.0 | Easy to dissolve in water |

Example 13

Example 13 comprises the steps of: weighing 1.0 g of piperphentonamine hydrochloride and 20 g of dextran-40 as excipient, placing them into a flask and adding 600 ml of water for injection with pH 3.0 adjusted by hydrochloric acid, homogenizing. Raising the temperature up to 65° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the lyophilizing chamber, then decreasing the temperature to −35° C. for pre-freezing for 4 hours, then increasing the temperature to −20° C. for drying for 15 hours, again increasing the temperature to 20° C. for drying for 5 hours. The properties of the resulted product are as follows:

| Detection Items | | | | |
|---|---|---|---|---|
| Appearance | pH | Color | Clarity | Solubility |
| White, loose cake, hardly changing shape and shrinkage | 3.5 | YG1-2 | 1.0 | Easy to dissolve in water |

Example 14

Example 14 comprises the steps of: weighing 1.0 g of piperphentonamine hydrochloride and 2.5 g of lactose as excipient, adding 400 ml of water for injection with pH 2.0 adjusted by hydrochloric acid solution. Raising the temperature up to 45° C. and ultrasonic dissolving until the materials fully dissolved (about 10 minutes), degerming by positive pressure filtering using stainless steel filter, split charging by 5 ml per vial, and half covering with a special rubber plug for lyophilization. Decreasing the temperature of the sample chamber to −35° C., then placing the samples into it for pre-freezing for 3 hours, then increasing the temperature to −20° C. for freeze dehydrating for 25 hours, again increasing the temperature to 30° C. for drying for 5 hours. The properties of the resulted product are as follows:

| | Detection Items | | | |
|---|---|---|---|---|
| Appearance | Color and luster | Solubility | Clarity | Moisture content (%) |
| Whole loose cake | white | Easy to dissolve in 30 seconds | 0.5 | 2.6 |

Example 15

Example 15 comprises the steps of: weighing 1.0 g of piperphentonamine hydrochloride and 10.0 g of lactose as excipient, adding 500 ml of water for injection with pH 2.5 adjusted by 1N hydrochloric acid solution. Raising the temperature up to 55° C. and ultrasonic dissolving until the materials fully dissolved (about 10 minutes), degerming by positive pressure filtering using stainless steel filter, split charging by 5 ml per vial, and half covering with a special rubber plug for lyophilization. Decreasing the temperature of the sample chamber to −25° C., then placing the samples into it for pre-freezing for 7 hours, then increasing the temperature to −10° C. for freeze dehydrating for 15 hours, again increasing the temperature to 20° C. for drying for 15 hours. The properties of the resulted product are as follows:

| | Detection Items | | | |
|---|---|---|---|---|
| Appearance | Color and luster | clarity | Solubility | Moisture content (%) |
| Whole loose cake | White | 0.5 | Easy to dissolve in 30 seconds | 2.4 |

Example 16

Example 16 comprises the steps of: weighing 1.0 g of piperphentonamine hydrochloride and 20.0 g of lactose as excipient, adding water for injection with pH 3.0 adjusted by hydrochloric acid solution to 500 ml. Raising the temperature up to 60° C. and ultrasonic dissolving until the materials fully dissolved (about 10 minutes), degerming by positive pressure filtering using stainless steel filter, split charging by 5 ml per vial, half covering with a special rubber plug for lyophilization. Decreasing the temperature of the sample chamber to −30° C., then placing the samples into it for pre-freezing for 5 hours, then increasing the temperature to −15° C. for freeze dehydrating for 20 hours, again increasing the temperature to 25° C. for drying for 10 hours. The properties of the resulted product are as follows:

| | Detection Items | | | |
|---|---|---|---|---|
| Appearance | Color and luster | Clarity | Solubility | Moisture content (%) |
| Whole loose cake | white | 0.5 | Easy to dissolve in 30 seconds | 2.4 |

Example 17

Example 17 comprises the steps of: weighing 1.0 g of piperphentonamine hydrochloride and 25 g of lactose as excipient, adding 600 ml of water for injection with pH 4.5 adjusted by disodium hydrogen phosphate-potassium dihydrogen phosphate buffer. Raising the temperature up to 75° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the samples into the sample chamber and decreasing the temperature to −25° C. for pre-freezing for 2 hours, then increasing the temperature to −20° C. for freeze dehydrating for 15 hours, again increasing the temperature to 20° C. for drying for 5 hours. The properties of the resulted product are as follows:

| | Detection Items | | | |
|---|---|---|---|---|
| Appearance | Color and luster | Clarity | Solubility | Moisture content (%) |
| Whole loose cake | White | 0.5 | Easy to dissolve in 30 seconds | 2.4 |

Example 18

Example 18 comprises the steps of: weighing 1.0 g of piperphentonamine hydrochloride and 10.0 g of lactose as excipient, adding 500 ml of water for injection with pH 5.5 adjusted by disodium hydrogen phosphate-potassium dihydrogen phosphate buffer. Raising the temperature up to 90° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the sample chamber, then decreasing the temperature to −25° C. for pre-freezing for 4 hours, then increasing the temperature to −20° C. for freeze dehydrating for 15 hours, again increasing the temperature to 30° C. for drying for 15 hours. The properties of the resulted product are as follows:

| Detection Items | | | | |
|---|---|---|---|---|
| Appearance | Color and luster | Clarity | Solubility | Moisture content (%) |
| whole loose cake | white | 0.5 | Easy to dissolve in 30 seconds | 2.4 |

Example 19

Example 19 comprises the steps of: weighing 1.0 g of piperphentonamine hydrochloride and 30.0 g of PEG1500 as excipient, placing them into a flask and adding 500 ml of water for injection with pH 2.0 adjusted by 1N hydrochloric acid solution, homogenizing. Raising the temperature up to 50° C. and ultrasonic dissolving until the materials fully dissolved (about 10 minutes), degerming by positive pressure filtering using stainless steel filter, split charging by 5 ml per vial, and half covering with a special rubber plug for lyophilization. Decreasing the temperature of the sample chamber to −30° C., then placing the samples into it for pre-freezing for 5 hours, then increasing the temperature to −20° C. for freeze dehydrating for 20 hours, again increasing the temperature to 25° C. for drying for 10 hours. The properties of the resulted product are as

| Detection Items | | | | | |
|---|---|---|---|---|---|
| Appearance | Color and luster | Color | Clarity | Solubility | pH |
| Whole loose cake | White | YG1-2 | 0.5 | Easy to dissolve in water | 2.8 |

Example 20

Example 20 comprises the steps of: weighing 1.0 g of piperphentonamine hydrochloride and 2.5 g of PEG4000 as excipient, placing them into a flask and adding 500 ml of water for injection with pH 2.5 adjusted by 1N hydrochloric acid solution. Raising the temperature up to 60° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the sample chamber, then decreasing the temperature of the sample chamber to −25° C. for pre-freezing for 3 hours, then increasing the temperature to −15° C. for freeze dehydrating for 20 hours, again increasing the temperature to 25° C. for drying for 10 hours. The properties of the resulted product are as follows: shaped, excellent appearance, not changing shape by a fillip with slightly forcing, easy to dissolve, clear and color YG1-2.

Example 21

Example 21 comprises the steps of: weighing 1.0 g of piperphentonamine hydrochloride and 2.5 g of PEG6000 as excipient, placing them into a flask and adding 600 ml of water for injection with pH 5.5 adjusted by disodium hydrogen phosphate-sodium dihydrogen phosphate buffer. Raising the temperature up to 60° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the sample chamber, then decreasing the temperature of the sample chamber to −25° C. for pre-freezing for 3 hours, then increasing the temperature to −15° C. for freeze dehydrating for 20 hours, again increasing the temperature to 25° C. for drying for 10 hours. The properties of the resulted product are as follows: shaped, excellent appearance, not changing shape by a fillip with slightly forcing, easy to dissolve, clear and color YG1-2.

Example 22

Example 22 comprises the steps of: weighing 1.0 g of piperphentonamine hydrochloride and 20 g of PEG4000 as excipient, placing them into a flask and adding 500 ml of water for injection with pH 2.5 adjusted by 1N hydrochloric acid solution. Raising the temperature up to 60° C. and ultrasonic dissolving until the materials fully dissolved (about 10 minutes), degerming by positive pressure filtering using stainless steel filter, split charging by 5 ml per vial, and half covering with a special rubber plug for lyophilization. Placing the split charged samples into the sample chamber, then decreasing the temperature of the sample chamber to −25° C. for pre-freezing for 3 hours, then increasing the temperature to −15° C. for freeze dehydrating for 20 hours, again increasing the temperature to 25° C. for drying for 10 hours. The properties of the resulted product are as follows: shaped, excellent appearance, not changing shape by a slightly forcing fillip, easy to dissolve, clear and color YG1-2.

Example 23

Example 23 comprises the steps of: weighing 1.0 g of piperphentonamine hydrochloride and 2.5 g of Poloxamer as excipient, placing them into a flask and adding 500 ml of water for injection with pH 2.0 adjusted by o-phthalic acid-hydrochloric acid buffer. Raising the temperature up to 40° C. and ultrasonic dissolving until the materials fully dissolved (about 10 minutes), degerming by positive pressure filtering using stainless steel filter, split charging by 5 ml per vial, and half covering with a special rubber plug for lyophilization. Decreasing the temperature of the sample chamber to −30° C., then placing the samples into it for pre-freezing for 5 hours, then increasing the temperature to −20° C. for freeze dehydrating for 20 hours, again increasing the temperature to 25° C. for drying for 10 hours. The properties of the resulted product are as follows:

| Detection Items | | | | |
|---|---|---|---|---|
| Appearance | pH | Color | Clarity | Solubility |
| White, whole loose cake | 2.5 | YG1-2 | 0.5 | Easy to dissolve in water |

Example 24

Example 24 comprises the steps of: weighing 1.0 g of piperphentonamine hydrochloride and 25.0 g of Poloxamer as excipient, placing them into a flask and adding 400 ml of water for injection with pH 3.5 adjusted by acetic acid-ammonium acetate buffer. Raising the temperature up to 60° C. and ultrasonic dissolving until the materials fully dissolved (about 10 minutes), degerming by positive pressure filtering using stainless steel filter, split charging by 5 ml per vial, half covering with a special rubber plug for lyophilization. Placing the split charged samples into the sample chamber, then decreasing the temperature of the sample chamber to −25° C. for pre-freezing for 3 hours, then increasing the temperature to −15° C. for freeze dehydrating for 20 hours, again increasing the temperature to 25° C. for drying for 10 hours. The properties of the resulted product are as follows: shaped, excellent appearance, not changing shape by a fillip with slightly forcing, easy to dissolve, clear and color YG1-2.

Example 25

Example 25 comprises the steps of: weighing 1.0 g of piperphentonamine hydrochloride and 30.0 g of Poloxamer as excipient, placing them into a flask and adding 600 ml of water for injection with pH 5.0 adjusted by acetic acid-potassium acetate buffer. Raising the temperature up to 90° C. and ultrasonic dissolving until the materials fully dissolved (about 10 minutes), degerming by positive pressure filtering using stainless steel filter, split charging by 5 ml per vial, half covering with a special rubber plug for lyophilization. Placing the split charged samples into the sample chamber, then decreasing the temperature of the sample chamber to −25° C. for pre-freezing for 3 hours, then increasing the temperature to −15° C. for freeze dehydrating for 20 hours, again increasing the temperature to 25° C. for drying for 10 hours. The properties of the resulted product are as follows: shaped, excellent appearance, not changing shape by a fillip with slightly forcing, easy to dissolve, clear and color YG1-2.

Example 26

Example 26 comprises the steps of: weighing 1.0 g of piperphentonamine hydrochloride and 10 g of glycine as excipient, placing them into a flask and adding 500 ml of water for injection with pH 3.0 adjusted by 1N hydrochloric acid solution, homogenizing. Raising the temperature up to 60° C. and ultrasonic dissolving until the materials fully dissolved (about 10 minutes), degerming by positive pressure filtering using stainless steel filter, split charging by 5 ml per vial, half covering with a special rubber plug for lyophilization. Placing the split charged samples into the sample chamber, then decreasing the temperature of the sample chamber to −25° C. for pre-freezing for 3 hours, then increasing the temperature to −15° C. for freeze dehydrating for 20 hours, again increasing the temperature to 25° C. for drying for 10 hours. The properties of the resulted product are as follows: shaped, excellent appearance, not changing shape by a fillip with slightly forcing, easy to dissolve, clear and color YG1-2.

Example 27

Example 27 comprises the steps of: weighing 1.0 g of piperphentonamine hydrochloride and 30.0 g of glycine as excipient, placing them into a flask and adding water for injection with pH 5.5 adjusted by acetic acid-potassium acetate buffer to 600 ml. Raising the temperature up to 90° C. and ultrasonic dissolving until the materials fully dissolved (about 10 minutes), degerming by positive pressure filtering using stainless steel filter, split charging by 5 ml per vial, half covering with a special rubber plug for lyophilization. Decreasing the temperature of the sample chamber to −30° C., then placing the split charged samples into it for pre-freezing for 5 hours, then increasing the temperature to −20° C. for freeze dehydrating for 20 hours, again increasing the temperature to 25° C. for drying for 10 hours. The properties of the resulted product are as follows: shaped, excellent appearance, not changing shape by a fillip with slightly forcing, easy to dissolve, clear and color YG1-2.

Example 28

Example 28 comprises the steps of: packing the piperphentonamine hydrochloride freeze-dried powders for injection prepared by any one of preparation methods in the above described Example 1 to 27 into the brown bottles with the special bottle plugs made of butyl rubber for lyophilization. Under the conditions of high temperature (40° C.) and strong light (4200Lx), taking samples for test on the 5th and 10th day respectively. The test results are shown below:

| | The results of the influencing factors for piperphentonamine hydrochloride lyophilized powder for injection | | | | |
|---|---|---|---|---|---|
| | Time (day) | | | | |
| | 0 | 5 | | 10 | |
| Condition | Normal temperature, daylight | 40° C. | 4200 Lx | 40° C. | 4200 Lx |
| Appearance | White freeze-dried powder | White freeze-dried powder | White freeze-dried powder | White freeze-dried powder | White freeze-dried powder |
| Color of solution | YG1 | YG1-2 | YG1-2 | YG1-2 | YG1-2 |
| Clarity | Acceptable | Acceptable | Acceptable | Acceptable | Acceptable |
| pH | 2.0-5.5 | Not significantly changed | Not significantly changed | Not significantly changed | Not significantly changed |
| Moisture content | 1.0%-3.0% | Not significantly changed | Not significantly changed | Not significantly changed | Not significantly changed |

-continued

The results of the influencing factors for piperphentonamine hydrochloride lyophilized powder for injection

|  | Time (day) | | | | |
|---|---|---|---|---|---|
|  | 0 | | 5 | | 10 |
| Related substances | Acceptable | Acceptable | Acceptable | Acceptable | Acceptable |
| Nominal content | 104.8% 104.3% | 104.0% 103.5% | 100.7% 102.2% | 103.9% 102.9% | 103.8% 104.8% |

Note:
the clarity is specified as no more than that of No. 3 standard turbid solution (Chinese Pharmacopoeia 2005, Part II, Appendix IX B); the individual related substance is not more than 1%, and the total related substances is not more than 2%.

Example 29

Example 29 comprises the steps of: packing the piperphentonamine hydrochloride freeze-dried powders for injection prepared by any one of the preparation methods in the above described Example 1 to 27 into brown bottles with the special bottle plugs made of butyl rubber for lyophilization. Observing the stability by the accelerated test, testing the appearances, the clarities of the solution, pH, moisture contents, related substances and contents after the products being placed at temperature of 40° C. and related humidity of 75% for 0, 1, 2, 3, and 6 months. The test results are shown below:

|  | Time (month) | | | | |
|---|---|---|---|---|---|
|  | 0 | 1 | 2 | 3 | 6 |
| Appearance | White freeze-dried powder | White freeze-dried powder | White freeze-dried powder | White freeze-dried powder | White freeze-dried powder |
| Color of solution | Comparable to YG1 | Comparable to YG1 | between YG1 and YG2 | between YG1 and YG2 | between YG1 and YG2 |
| Clarity | Acceptable | Acceptable | Acceptable | Acceptable | Acceptable |
| pH | 2.0-5.5 | 2.0-5.5 | 2.0-5.5 | 2.0-5.5 | 2.0-5.5 |
| Moisture Content(%) | 1.0-4.0 | 1.0-4.0 | 1.0-4.0 | 1.0-4.0 | 1.0-4.0 |
| Impurity from degradation | Individual < 1.0%; total < 2.0% | Individual 1.0%; total < 2.0% | Individual < 1.0%; total < 2.0% | Individual < 1.0%; total < 2.0% | Individual < 1.0%; total < 2.0% |
| Nominal content | 103.8% 104.2% | 103.9% 102.5% | 104.0% 103.4% | 101.6% 101.7% | 102.7% 104.1% |

Example 30

This example relates to the calcium sensitization experiments of the piperphentonamine hydrochloride lyophilized powder for injection (Piperphentonamine hydrochloride for injection, PPTA-I)

The effect of PPTA-I on the affinity of $Ca^{2+}$ to cTnC isolated from cattle cardiac muscle was studied by fluorescent probe dansyl chloride labeling to discuss the calcium sensitization mechanisms of piperphentonamine hydrochloride, and compared the results to the already known calcium sensitizers MCI-154 and sulmazole (Sul). The results show that PPTA-I increase the affinity of cTnC to $Ca^{2+}$ obviously and dose-dependently. By contrast, 50 μmol/L of MCI-154 and Sul showed no significant influence on the affinity curve of cTnC to $Ca^{2+}$. The results indicate that the calcium sensitizing mechanism of PPTA-I may be mediated by increasing the affinity of cTnC to $Ca^{2+}$ directly.

The Effect of PPTA-I on the Affinity Curve of cTnC to $Ca^{2+}$

The cTnC-$Ca^{2+}$ affinity curve is shifted to the left by characteristic of dose-dependent of piperphentonamine hydrochloride: slightly shifted to the left without statistical significance at 15 μmol/L, shifted to the left with statistical significance at 35 μmol/L; and shifted more significantly at 55 μmol/L by 0.2 pCa to the left compared with the control curve (FIG. 3), 55 μmol/L of MCI-154 or Sul showed no significant effect on the cTnC-$Ca^{2+}$ affinity curve (FIG. 4).

PPTA-I increasing the affinity of cTn C to $Ca^{2+}$ dose-dependently explains the calcium sensitivity of the PPTA-I on molecular level, implying that this effect may be one pathway that PPTA-I increasing myocardial calcium sensitivity and thereby promoting the myocardial contractility.

Sul and MCI-154 are well-established calcium sensitizers, but their special calcium sensitization mechanisms have still not been totally clear. The present experiment did not demonstrate their direct action of increasing the affinity of cTn C to $Ca^{2+}$, as described by the literatures, suggesting the calcium sensitization effect of Sul or MCI-154 is different from that of PPTA-I in that it achieves this effect otherwise rather than increasing the affinity of cTn C to $Ca^{2+}$ directly.

Example 31

This example relates to the experiment for the effect of PPTA-I on potassium channel of vascular smooth muscle.

For further studying the mechanism underlying the vasodilative effect of PPTA-I, the effect of PPTA-I on the current of calcium-sensitive potassium channel in smooth muscle cells of rabbit mesentery resistance vessel was investigated by whole-cell patch clamp technique. The results showed that 0.12 μmol/L PPTA-I significantly increased the current of the calcium-sensitive potassium channel and the current recovered to baseline after washing; PPTA-I dose-dependently increased the current of the calcium-sensitive potassium channel in the concentration range from 0.012 to 12 μmol/L.

Conclusions: PPTA-I increases the current of calcium sensitive potassium channel in vascular smooth muscle cells dose-dependently and reversibly.

Example 32

This example relates to the experiment for the therapeutic effect of the piperphentonamine hydrochloride for injection (PPTA-I) on heart failure.

To study the therapeutic effect of the novel cardiotonic and vasodilator PPTA-I on heart failure, the cardiac hemodynamic parameters were determined by a polygraph in cat heart failure model induced by verapamil. The results showed that 4 or 8 mg/kg of PPTA-I administered intravenously slightly decreased heart rate (HR) and blood pressure (BP), it also decreased the decline rate of left ventricular pressure (−dP/dt max), but not changing the left ventricular systolic pressure (LVSP), end-diastolic pressure (LVEDP) and rise rate of left ventricular pressure (+dP/dt max). The myocardial contractility was also improved by the PPTA-I in animals with heart failure, a similar effect to that of Milrinone. This study indicated that the contractile function is improved in cat heart failure model induced by verapamil.

TABLE 1

Cardiac hemodynamic parameters in Cat heart failure model induced by verapamil. (N = 12)

|  | Before heart failure | After heart failure | |
| --- | --- | --- | --- |
|  | Value | Value | Change (%) |
| HR, bpm | 131 ± 44 | 68 ± 24 *** | −46 ± 14 *** |
| MAP#, mmHg | 115 ± 34 | 69 ± 25 ** | −39 ± 13 *** |
| LVSP, mmHg | 148 ± 41 | 93 ± 27 ** | −36 ± 9 *** |
| LVEDP, mmHg | 8 ± 7 | 10 ± 9 | 55 ± 87 * |
| +dP/dt max, mmHg/s | 8250 ± 3750 | 3817 ± 1755 ** | −52 ± 11 *** |
| −dP/dt max, mmHg/s | 3750 ± 2494 | 1904 ± 815 * | −34 ± 37 ** |
| Cardiac contractility, g | 97 ± 37 | 63 ± 28 * | −35 ± 13 *** |

MAP: Mean arterial pressure
* P < 0.05
** P < 0.01
*** P < 0.001 vs. before heart failure.

The Effect of PPTA-I on the Current of the Calcium-Sensitive Potassium Channel

The perfusion was paused under whole-cell patch clamp mode, adding equal volume of solvent control at first for recording the current curve 3 minutes thereafter, and then adding 0.12 μmol/L of PPTA-I for same recording, the current curve of the latter showed a significant increase of outward current. Washed by perfusate for 3 minutes, the current curve was returned to baseline level. It demonstrated that the current-voltage relation curves are significantly different between before and after administration by t test (FIG. 5).

The perfusion was paused under whole-cell patch clamp mode and voltage clamping, adding targeted concentrations of PPTA-I ($1.2 \times 10^{-8}$ ~ $1.2 \times 10^{-5}$ mol/L) to the cell well by cumulating concentrations, recording the current curve of each concentration. The administering interval is 3 minutes. The result showed that PPTA-I increases the current significantly and dose-dependently. (FIG. 6)

Therapeutic Effects of PPTA-I (1) Effects on Heart Rate (HR), Blood Pressure (BP) and Cardiac Contractility PPTA-I 4 mg/kg administered intravenously slightly decreased the HRs and BPs in cats with heart failure. The HR and MAP were decreased by 16±7% and 14±10% compared with those of before administration respectively for a time period of 10 to 15 minutes. The effects were not further increased by increasing the dose to 8 mg/kg. Two minutes after 4 mg/kg of PPTA-I administered, the cardiac contractility was increased by 30±21% compared with baseline and increased by 57±53% at most after 8 mg/kg administered.

Milrinone 0.1 mg/kg did not affect HRs in cats with cardiac failure, and decreased the MAP by 10% and increased the cardiac contractility by 92±180% compared with baseline for a period of only 5 minutes (Table 2).

TABLE 2

The effects of PPTA-I on HR, BP and cardiac contractility
in cat cardiac failure model induced by verapamil.

|  | Solvent | PPTA-I mg/kg | | Milrinone |
|---|---|---|---|---|
| Time min | 0.8 ml/kg N = 6 | 4 N = 9 | 8 N = 9 | 0.1 mg/kg N = 9 |
| HR | | | | |
| Baseline, bpm | 90 ± 24 | 65 ± 25 | 54 ± 21 | 41 ± 20 |
| Change % | | | | |
| 2 | −1 ± 3 | 11 ± 11 * | 9 ± 9 * | 0 ± 5 |
| 5 | −3 ± 4 | −15 ± 15 * | −15 ± 17 * | 2 ± 15 |
| 10 | 3 ± 5 | −16 ± 7 *** ## | −17 ± 21 * | 2 ± 16 |
| 15 | −3 ± 4 | −12 ± 7 *** # | −21 ± 18 ** | 3 ± 16 |
| 20 | −4 ± 4 | −9 ± 6 ** | −22 ± 20 ** | −13 ± 37 |
| MAP | | | | |
| Baseline, mmHg | 67 ± 13 | 76 ± 27 | 66 ± 24 | 51 ± 20 |
| Change % | | | | |
| 2 | −1 ± 5 | −14 ± 10 ** # | −16 ± 12 ** # | −4 ± 4 * |
| 5 | −1 ± 6 | −11 ± 8 *** # | −16 ± 14 ** # | −10 ± 8 ** # |
| 10 | 0 ± 4 | −13 ± 9 *** ## | −16 ± 17 * | −10 ± 6 *** ## |
| 15 | 0 ± 7 | −10 ± 11 ** | −18 ± 13 ** # | −10 ± 8 ** # |
| 20 | −2 ± 5 | −2 ± 17 | −14 ± 13 ** | −8 ± 12 |
| Cardiac contractility | | | | |
| Baseline, g | 70 ± 41 | 36 ± 17 | 34 ± 26 | 35 ± 29 |
| Change % | | | | |
| 2 | −2 ± 5 | 30 ± 21 ** ## | 50 ± 54 * # | 38 ± 32 ** # |
| 5 | −3 ± 3 | 30 ± 36 * | 57 ± 53 ** # | 92 ± 80 ** # |
| 10 | 4 ± 7 | 4 ± 31 | 50 ± 61 * | 71 ± 78 * |
| 15 | 1 ± 13 | −5 ± 49 | 30 ± 48 | 58 ± 74 * |
| 20 | 5 ± 8 | 21 ± 83 | 19 ± 51 | 61 ± 69 * |

* $P < 0.05$
** $P < 0.01$
*** $P < 0.001$ vs. baseline
$P < 0.05$
$P < 0.01$ vs. solvent control (2) The Effect on Left Ventricular Pressure PPTA-I 4 mg/kg administered increased LVSP by 10±9% (P<0.01) and decreased +dP/dt max by 22±32% (P<0.05) compared with baselines, but without significant difference compared to solvent control. −dP/dt max was decreased by 35±12% at most after administration and lasted for 20 minutes, with significant difference compared to the solvent control. PPTA-I 8 mg/kg did not affect the LVSP, LVEDP and ±dP/dt max in cat cardiac failure model induced by verapamil. Milrinone 0.1 mg/kg increased +dP/dt max by 61±26% at most for a period over 20 minutes, but without changing LVSP, LVEDP and −dP/dt max in cats with cardiac failure (Table 3 and 4)

TABLE 3

The effect of PPTA-I on left ventricular pressure
in cat cardiac failure model induced by verapamil

|  | Solvent | PPTA-I mg/kg | | Milrinone |
|---|---|---|---|---|
| Time min | 0.8 ml/kg N = 6 | 4 N = 9 | 8 N = 9 | 0.1 mg/kg N = 9 |
| LVSP | | | | |
| Baseline, mmHg | 86 ± 16 | 107 ± 38 | 102 ± 39 | 85 ± 25 |
| Change, % | | | | |
| 2 | 5 ± 7 | 6 ± 6 ** | −2 ± 7 | 4 ± 11 |
| 5 | 5 ± 7 | 10 ± 9 ** | −1 ± 12 | 5 ± 15 |

TABLE 3-continued

The effect of PPTA-I on left ventricular pressure
in cat cardiac failure model induced by verapamil

|  | Solvent | PPTA-I mg/kg | | Milrinone |
|---|---|---|---|---|
| Time min | 0.8 ml/kg N = 6 | 4 N = 9 | 8 N = 9 | 0.1 mg/kg N = 9 |
| 10 | 6 ± 8 | 0 ± 14 | −4 ± 15 | 6 ± 17 |
| 15 | 6 ± 7 | −1 ± 14 | −9 ± 14 | 3 ± 18 |
| 20 | 6 ± 7 | −2 ± 27 | −3 ± 10 | 4 ± 22 |
| LVEDP | | | | |
| Baseline, mmHg | 7 ± 6 | 13 ± 9 | 17 ± 9 | 17 ± 9 |
| Change, % | | | | |
| 2 | −1 ± 12 | 3 ± 13 | 9 ± 18 | 1 ± 2 |
| 5 | −1 ± 12 | 2 ± 21 | 23 ± 40 | 5 ± 16 |
| 10 | 3 ± 9 | 5 ± 19 | 17 ± 35 | −1 ± 5 |
| 15 | −3 ± 17 | 2 ± 11 | 4 ± 37 | −7 ± 16 |
| 20 | 3 ± 9 | 11 ± 8 ** | 9 ± 40 | 2 ± 11 |

** $P < 0.01$ vs. baseline

TABLE 4

The effect of PPTA-I on left ventricular dp/dt max
in cat cardiac failure model induced by verapamil

| Time min | Solvent 0.8 ml/kg N = 6 | PPTA-I mg/kg 4 N = 9 | 8 N = 9 | Milrinone 0.1 mg/kg N = 9 |
|---|---|---|---|---|
| +dP/dt max | | | | |
| Baseline, mmHg/s | 4467 ± 1148 | 4061 ± 1997 | 3372 ± 1845 | 1917 ± 1094 |
| | | Change, % | | |
| 2 | −1 ± 7 | 6 ± 27 | 3 ± 22 | 18 ± 23 * |
| 5 | −1 ± 7 | 5 ± 30 | 1 ± 40 | 52 ± 24 *** ### |
| 10 | 3 ± 6 | −17 ± 27 * | −1 ± 42 | 61 ± 26 *** ### |
| 15 | 2 ± 7 | −22 ± 32 * | −7 ± 49 | 54 ± 33 *** ## |
| 20 | 2 ± 8 | −6 ± 49 | −7 ± 40 | 61 ± 45 ** # |
| −dP/dt max | | | | |
| Baseline, mmHg/s | 2417 ± 639 | 1900 ± 866 | 1306 ± 693 | 956 ± 495 |
| | | Change, % | | |
| 2 | 1 ± 9 | −14 ± 16 * | −12 ± 17 | 0 ± 23 |
| 5 | −3 ± 4 | −9 ± 32 | 10 ± 51 | 3 ± 19 |
| 10 | 1 ± 7 | −26 ± 23 ** # | 20 ± 85 | 11 ± 20 |
| 15 | −1 ± 5 | −24 ± 18 ** ## | −9 ± 41 | 8 ± 23 |
| 20 | −1 ± 8 | −35 ± 12 *** ## | 3 ± 26 | −4 ± 22 |

\* P < 0.05
\*\* P < 0.01
\*\*\* P < 0.001 vs. baseline
\# P < 0.05
\#\# P < 0.01
\#\#\# P < 0.001 vs. solvent control (3) Conclusions PPTA-I slightly decreases the HR and BP in cat heart failure model induced by verapamil, and significantly increase the myocardial contractility and +dP/dt max, indicating that PPTA-I has the effect for improving cardiac function.

Example 33

This example relates to the experiment for cardioprotection effect of the piperphentonamine hydrochloride for injection (PPTA-I).

In order to further evaluate the protective effect of PPTA on myocardium injured by ischemia-reperfusion, a pathological model of myocardial ischemia-reperfusion injury in cats in vivo was established by arrest the coronary artery for 30 min, then reperfusion for 60 min, studying the effects on blood biochemistry, myocardium ultrastructure, etc.

The serum biochemistry results showed that PPTA-I 1.2 to 4.8 mg/kg could antagonize dose-dependently the increase of the final product of lipid-peroxidation malonaldehyde (MDA) produced by ischemia-reperfusion, decrease the activity of creatine phosphokinase (CPK) and the amount of Troponin-I (TnI). The result of myocardium ultrastructure showed that the PPTA-I significantly protect against myocardial injury. The results are shown in Table 5.

TABLE 5

The effects of PPTA-I on serum indices and myocardial injury
in myocardial ischemia-reperfusion cats

| Group | Drug mg/kg | n | Content of MDA, nmol/L | CPK activity | Content of cTnI | Score of myocardium pathological change |
|---|---|---|---|---|---|---|
| sham operation | — | 4 | 31 ± 4.5 | 220 ± 6 | 0.31 ± 0.055 | 0 ± 0 |
| Injury control | — | 8 | 86 ± 17 | 385 ± 75 | 2.3 ± 0.62 | 2.5 ± 0.55 |
| Injury + PPTA-I | 1.2 | 6 | 74 ± 9.8 # | 300 ± 56 # | 1.5 ± 0.42 # | 2.0 ± 0.18 # |
| | 2.4 | 6 | 63 ± 10 ## | 263 ± 51 ## | 1.1 ± 0.28 ## | 1.2 ± 0.31 ## |
| | 4.8 | 6 | 55 ± 8.7 ## | 248 ± 48 ## | 0.68 ± 0.15 ## | 0.86 ± 0.22 ## |
| Injury + verapamil | 1.3 | 4 | 65 ± 12 ## | 271 ± 80 ## | 1.4 ± 0.21 ## | 1.3 ± 0.18 ## |

Conclusions:

It was observed on the pathological model of myocardial ischemia-reperfusion injury induced by arresting the coronary artery of cats that PPTA-I dose-dependently decreases the content of the final product of lipid-peroxidation malonaldehyde (MDA), decreases the activity of serum creatine phosphokinase (CPK) and the content of Troponin-I (TnI), and alleviates the injury of the myocardial ultrastructure. These further indicate that PPTA-I could protect heart from ischemia-reperfusion injury in vivo.

Example 34

This example relates to the clinical use of piperphentonamine hydrochloride for injection (PPTA-I) for treatment of heart failure and protection of injured myocardium. The dose for heart failure is 0.5 mg/kg, administered by intravenous bolus of 10% of the dose plus intravenous infusion of remained 90% of the dose. The treatment course is 7 days. The results are shown in Table 6. The dose for myocardial protection is 1.0 mg/kg, administered by intravenous infusion or adding into the cardioplegia liquid used in cardiosurgical operation for cardiac perfusion. The treatment course is 7 days as well. The results are shown in Table 7.

TABLE 6

The clinical efficacies of PPTA-I on acute and chronic cardiac dysfunction.

| | | Efficacy indices | | | | |
|---|---|---|---|---|---|---|
| Group | n | Decrease of pulmonary capillary wedge pressure, % | Increase of ejection fraction, % | Decrease of Brain natriuretic peptide, % | Symptom improvement, % | Total effective rate, % |
| Control | 15 | 5.2 ± 8.5 | 7.8 ± 9.6 | 10 ± 15 | 40 | 53 |
| PPTA-I | 45 | 35 ± 12 | 56 ± 23 | 41 ± 18 | 88.9 | 84 |

TABLE 7

The clinical efficacies of PPTA-I on myocardial injury in both of cardiac internal medicine and cardiac surgery.

| | | Efficacy indices | | | |
|---|---|---|---|---|---|
| Group | n | Increase of ejection fraction, % | Decrease of troponin, % | Symptom improvement, % | Total effective rate, % |
| Valve replacement control 1 | 20 | 48 ± 25 | 15 ± 10 | 100 | 90 |
| PPTA-I | 35 | 65 ± 26 | 48 ± 18 | 100 | 100 |
| Bypass surgery control 2 | 20 | 26 ± 15 | 8.9 ± 5.7 | 90 | 90 |
| PPTA-I | 35 | 43 ± 17 | 21 ± 9.4 | 100 | 100 |
| ACS control 3 | 30 | 31 ± 11 | 11 ± 13 | 87 | 83 |
| PPTA-I | 30 | 56 ± 24 | 42 ± 15 | 93 | 97 |

ACS: Acute Coronary Syndrome

CONCLUSION

The above results suggest that compared with the excipient control groups, the treatment effect of PPTA-I is obvious by improving the cardiac function significantly and alleviating the myocardial injury.

The invention claimed is:

1. A method for preparing the piperphentonamine hydrochloride lyophilized powder for injection, comprising the steps of: weighing the piperphentonamine hydrochloride and the excipient, adding 500 parts of water for injection, raising the temperature up to 60° C., ultrasonic dissolving, degerming and split charging into a glass bottle, decreasing the temperature of the sample chamber to −25° C.-−35° C., then placing the split charged sample into it for pre-freezing for 3-7 hours, increasing the temperature to −20° C.-−10° C. for freeze dehydrating for 15-25 hours, and again increasing the temperature to 20° C.-30° C. for drying for 5-15 hours.

2. A method for preparing the piperphentonamine hydrochloride lyophilized powder for injection of, comprising the steps of: weighing the piperphentonamine hydrochloride and the excipient, adding 500 parts of water for injection, raising the temperature up to 60° C., ultrasonic dissolving, degerming and split charging into a glass bottle, placing the split charged sample into the sample chamber, then decreasing the temperature of the sample chamber to −25° C.-−35° C. for pre-freezing for 2-4 hours, increasing the temperature to −20° C.-−10° C. for freeze dehydrating for 15-25 hours, and again increasing the temperature to 20° C.-30° C. for drying for 5-15 hours.

3. The method for preparing the piperphentonamine hydrochloride lyophilized powder for injection according to claim 1, wherein said degerming is filtering via positive pressure, and the glass bottle is brown.

4. The method for preparing piperphentonamine hydrochloride lyophilized powder for injection according to claim 2, wherein said degerming is filtering via positive pressure, and the glass bottle is brown.

* * * * *